(12) United States Patent
Huepenbecker et al.

(10) Patent No.: US 6,289,251 B1
(45) Date of Patent: Sep. 11, 2001

(54) HIGH STRENGTH MEDICAL ELECTRICAL LEAD

(75) Inventors: George M. Huepenbecker, Vadnais Heights; Timothy G. Laske, Shoreview, both of MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 09/430,890

(22) Filed: Nov. 1, 1999

(51) Int. Cl.[7] .................................................. A61N 1/05
(52) U.S. Cl. ..................... 607/122; 607/116; 600/374; 600/377
(58) Field of Search .................................. 607/122, 116, 607/119, 123, 126, 127, 128; 600/372, 373–375, 377, 393

(56) References Cited

U.S. PATENT DOCUMENTS

| | | |
|---|---|---|
| 5,231,996 | 8/1993 | Bardy et al. . |
| 5,246,014 | 9/1993 | Williams et al. . |
| 5,584,873 | 12/1996 | Shoberg et al. . |
| 5,676,694 | 10/1997 | Boser et al. . |
| 5,935,159 | * 8/1999 | Cross, Jr. et al. ................... 607/116 |
| 6,016,436 | * 1/2000 | Bischoff et al. ..................... 600/374 |
| 6,119,042 | * 10/2000 | Verness et al. ...................... 607/122 |

OTHER PUBLICATIONS

U.S. Patent Application, SN 08/938,269 filed Sep. 26, 1997, Bischoff et al, entitled Medical Electrical Lead.

* cited by examiner

*Primary Examiner*—Kennedy Schaetzle
(74) *Attorney, Agent, or Firm*—Beth L. McMahon

(57) ABSTRACT

An implantable electrical lead having at least two mutually insulated electrical components that are separated by a portion of the lead's body fabricated of a plant, extensible biocompatible insulated material. An extensible conductor extends from the proximal end of the lead body to a first one of the electrical components, and a second, inextensible conductor extends from the proximal end of the lead body to a second one of the electrical components. An inextensible reinforcement member is coupled to the inextensible conductor and extends distally from the second electrical component to the first electrical component and is coupled mechanically to the first electrical component.

8 Claims, 2 Drawing Sheets

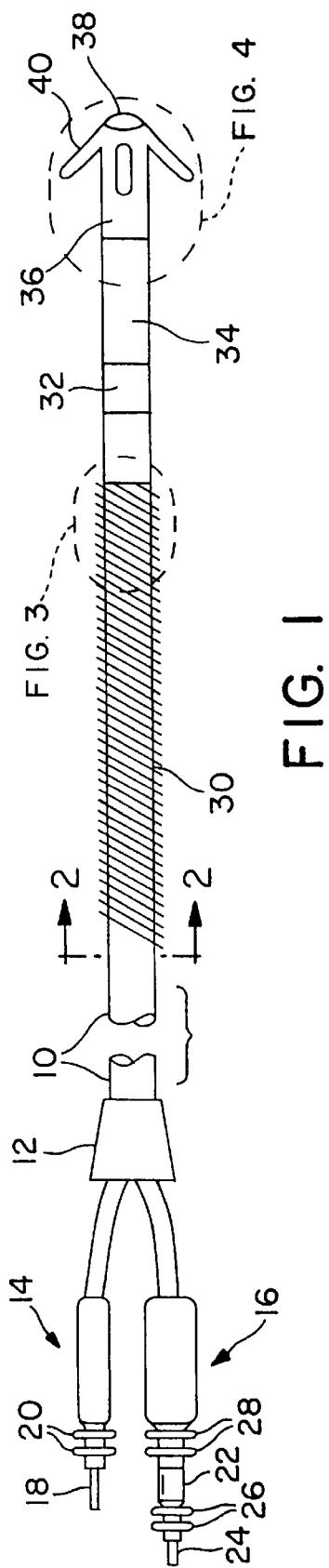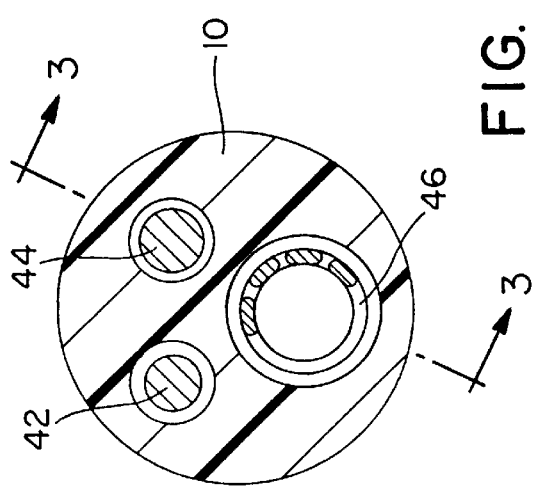

HIGH STRENGTH MEDICAL ELECTRICAL LEAD

BACKGROUND OF THE INVENTION

The present invention relates to implantable medical leads generally and more particularly to multi-conductor implantable leads employing coiled conductors that extend to a distal portion of the lead.

In the context of implantable pacing and cardioversion leaves, it is desirable that the lead be provided with a tensile member that extends along the entire length of the lead. Such a tensile member is desirable in that it prevents disassembly of the lead in response to traction forces applied to the proximal end of the lead, in conjunction with removal of the lead after implant. One approach to providing such a longitudinal reinforcement is set forth in U.S. Pat. No. 5,231,996 issued to Bardy et al, which suggests adding a nonconductive tensile reinforcing member from the connector assembly at the proximal end of the lead to an electrode located at the distal end of the lead. An alternative approach to providing a tensile member extending the length of the lead is set forth in U.S. patent application Ser. No. 08/938,269 by Bischoff et al., filed on Sep. 27, 1997, which discloses a structure in which the tip and ring electrode are mounted to a rigid plastic head and the conductor extending from the proximal end of the lead to the ring electrode is mechanically interconnected with the rigid plastic head. The disadvantage with the approach set forth in the Bardy et al patent is that it requires an additional tensile member extending the entire length of the lead, which in turn generally increases in the required diameter of the lead body over the majority of its length. Although the approach set forth in the above-cited Bischoff et al. application avoids the problem of an increased lead diameter, it requires a rigid member interconnecting the ring electrode and the tip electrode in order to provide tensile reinforcement all the way to the distal electrode. In the context of tined leads or other leads in which a coiled conductor is used to connect to the tip electrode and in which the portion of the lead body intermediate the tip electrode and electrodes located proximal thereto is typically fabricated out of a flexible elastomer, the approach of the Bischoff et al. application is not readily applicable.

SUMMARY OF THE INVENTION

The present invention is directed toward a provision of a pacing or cardioversion lead of the type having a distal or tip electrode and one or more electrodes located proximal to the tip electrode, separated therefrom by a flexible lead body segment, and having a coiled conductor extending from the proximal end of the lead to the tip electrode, permitting passage of a stylet. In such leads, the coiled conductor does not prevent stretching and breaking of the flexible lead body segment between the tip electrode and the electrode located most closely proximal thereto and has the potential for causing serious problems during attempted extractions of the lead, in that the coiled conductor is capable of significant longitudinal extension. The present invention provides a mechanism for providing a reinforcement extending the entire length of the lead body, in such a lead, without the disadvantage of an over-all increase in lead body diameter.

The present invention accomplishes the objects discussed above by means of a reinforcement member which is mechanically coupled to and extends distally from an inextensible conductor coupled to an electrode or sensor located proximal to the tip electrode, and which in turn is mechanically coupled to the tip electrode located at the distal end of the lead. The reinforcement member mechanically couples but does not electrically couple the inextensible conductor and the tip electrode. Because the reinforcement extends from the distal termination of a lead conductor, it can occupy the portion of the lead body that the lead conductor occupies in portions of the lead body proximal thereto, avoiding the necessity for an increased lead body diameter along the entire length of the lead. The reinforcement member is preferably non-conductive but may be conductive if insulated from the inextensible conductor to which it is coupled and/or from the distal or tip electrode. Limiting the reinforcement member to a distal portion of the lead also simplifies construction of the lead, in that it requires no additional interconnections to be made between the reinforcement member and the connector assembly at the proximal end of the lead. The reinforcement member is preferably coupled to the largest and/or strongest of the inextensible conductors within the lead body.

BRIEF DESCRIPTION OF THE DRAWINGS

FIG. 1 is a plan view of a lead according to the present invention.

FIG. 2 is a cross section through the lead body in the portion of the lead proximal to the coiled defibrillation electrode 60.

DETAILED DESCRIPTION OF THE EMBODIMENT

Figure 3:
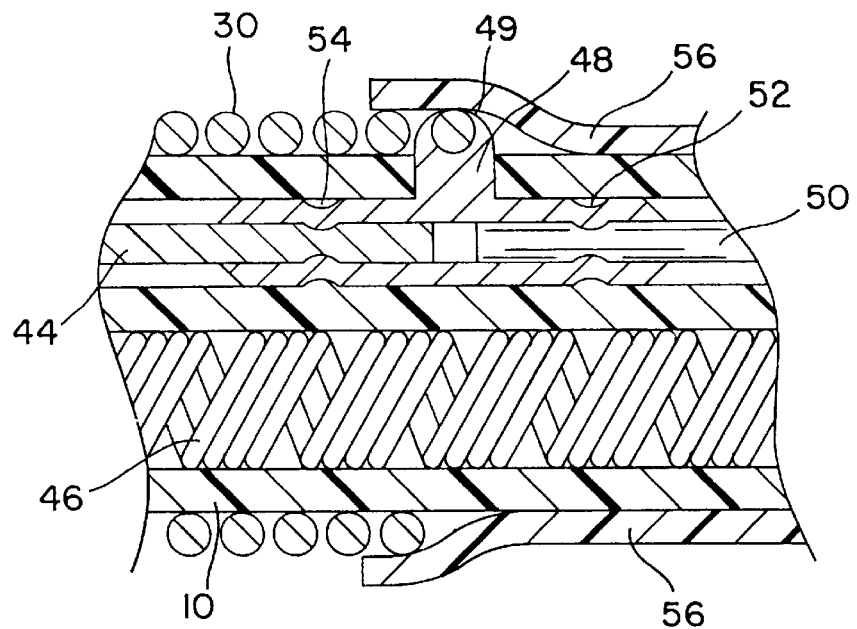
FIG. 3 illustrates a cross section of the lead taken in the vicinity of the distal end of defibrillation electrode 30.

FIG. 1 is a plan view of a lead according to the present invention. The lead is provided with an elongated insulative lead body 10, which terminates at its proximal extremity in a molded bifurcation member 12, from which two connector assemblies 14 and 16 extend. Connector assembly 14 carries a single connector pin 18 and associated sealing rings 20 for sealing the connector assembly in the bore of an implantable cardiac pacemaker/cardioverter/defibrillator. Connector assembly 16 carries a connector ring 22 and a connector pin 24 and associated sealing rings 26 and 28 for sealing the connector assembly. The distal portion of the lead body carries an elongated coiled defibrillation electrode 30, coupled to connector pin 18 internally by means of an elongated, inextensible stranded conductor. Located distal to defibrillation electrode 30 is a ring electrode 32, in turn coupled to connector ring 22 by a second, elongated, inextensible stranded conductor. At the distal end of the lead is a tip electrode 38 which is connected to connector pin 24 by an elongated, extensible, coiled conductor, configured so that a stylet may pass through connector pin 24 to the distal end of the lead at or adjacent electrode 38. Electrode 38 is provided with an internal electrode shank, around which insulative tine sleeve 36 is mounted. The lead is optionally provided with tines 40 to assist in acute fixation of the electrode 38 in the right ventricular apex. Separating tip electrode 38 and ring electrode 32 is a tip-ring spacer 34, which is, fabricated of a pliant elastomeric material such polyurethane or silicone rubber tubing.

FIG. 2 is a cross section through the lead body in the portion of the lead proximal to the coiled defibrillation electrode 30. In this view it can be seen that the lead body 10 is provided with three internal lumens carrying two inextensible, stranded conductors 42 and 44 which may correspond to the conductors disclosed in U.S. Pat. No. 5,246,014 issued to Williams et al or U.S. Pat. No. 5,584,873 issued to Shoberg et al, both of which are incorporated herein by reference in their entireties. Conductor 42 extends from connector pin 22 (FIG. 1) to ring electrode 32, and conductor 44 extends from connector pin 18 to defibrillation electrode 30. In the embodiment illustrated, conductor 44 has a greater diameter, as a result of its need for higher current carrying capabilities in conjunction with delivery of cardioversion and defibrillation pulse energies to electrode 30. Conductor 44 correspondingly has a higher tensile strength and is the conductor to which the nonconductor reinforcement member is coupled as illustrated in FIG. 3 below.

FIG. 3 illustrates a cross section of the lead taken in the vicinity of the distal end of defibrillation electrode 30. In this view, the interconnection of stranded conductor 44 and defibrillation electrode 30 is illustrated. These two elements of the lead are interconnected by means of a cross-groove crimp sleeve generally as described in U.S. Pat. No. 5,676,694, issued to Boser et al. and incorporated herein by reference in its entirety. Like the cross-groove crimp sleeve in the Boser et al. patent, cross-groove crimp sleeve 48 is provided with an elongated tubular section in which the distal termination of conductor 44 is located, and in which it is maintained by means of crimps 54. The crimp sleeve 48 is provided with a laterally extending projection, which carries a groove 49 in which the distal end of defibrillation electrode 30 is located and welded in order to provide a mechanical and electrical interconnection with conductor 44. Unlike the cross-groove crimp sleeve of the Boser et al. patent, the cylindrical portion of the crimp sleeve 48 extends distally to the laterally extending shoulder, providing a lumen in which tensile member 50 may be inserted and in which tensile member 50 is maintained by means of crimps 52.

Tensile member 50 may take the form of a monofilament or stranded cord fabricated of a high tensile strength, non-conductive plastic or fiber, for example, ultra-high molecular weight polyethylene or polyester. Tensile member 50 may also be adhesively coupled to the interior of cross-groove crimp sleeve 48, if desired. Tensile member 50 extends to and is mechanically connected to tip electrode 38 (FIG. 1) as illustrated in more detail in FIG. 4 discussed below. Alternatively, tensile member 50 may be conductive, although this will require an insulated connection with either conductor 44 or tip electrode 38. If the reinforcement is conductive, it may simply be an extension of conductor 44. By means of the interconnection between conductor 44 and tensile member 50, traction forces applied to the proximal end of the lead are communicated to tip electrode 38, located at the distal end of the lead, preventing stretching and/or tearing of the lead intermediate the defibrillation electrode 30 and the tip electrode 38.

Figure 4:
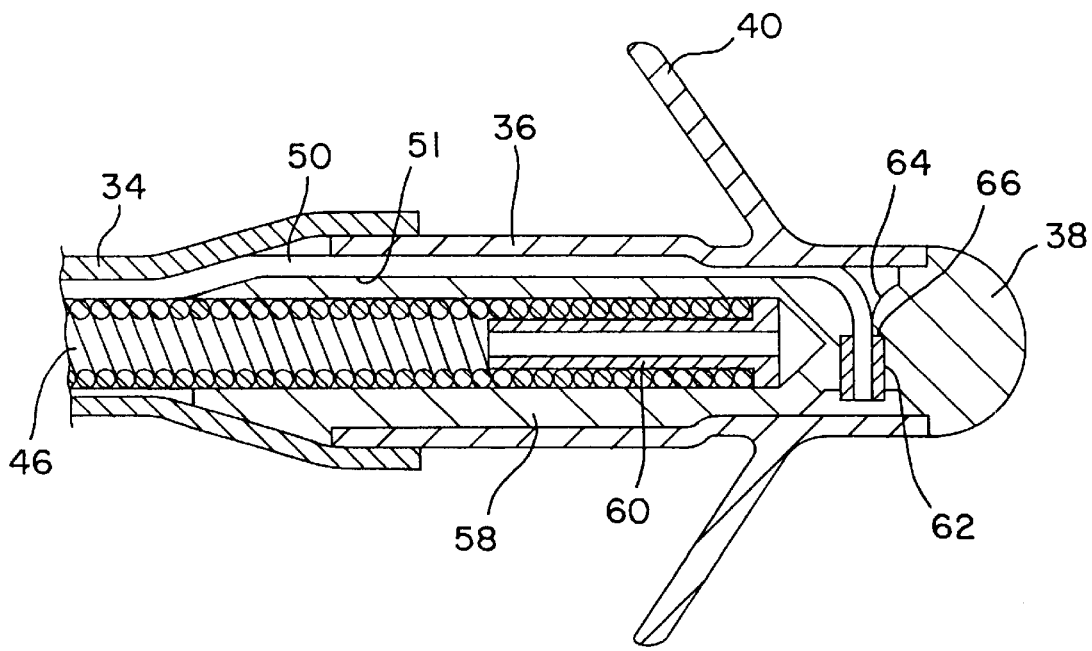
FIG. 4 illustrates a cross-section through the lead in the vicinity of tip electrode 38.

An outer insulative sleeve 56 covers the distal end of defibrillation coil electrode 30 and extends distally to abut the exposed portion of ring electrode 32 (FIG. 1). Lead body 10 extends distally from defibrillation electrode 30 to ring electrode 32, where the lead body structure transitions from the multi-lumen structure illustrated in FIG. 2 to a single lumen tube, as illustrated in FIG. 4, discussed below as is common in present commercially marketed multi-conductor leads. Distal to the ring electrode 32, reinforcement member 50 and coiled conductor 46 extend within this single lumen tube, which makes up the tip-ring spacer 34.

FIG. 4 illustrates a cross-section through the lead in the vicinity of tip electrode 38. In this view, it can be seen that tip-ring spacer 34 takes the form of a tube of biocompatible plastic such as polyurethane or silicone rubber, and surrounds the reinforcement member 50 and the coiled conductor 46. In this view it can be seen that insulative tine sleeve 36 is provided with a proximally extending inner shank portion 58 comprising an internal lumen in which the distal end of coiled connector 46 is maintained by crimping core 60 and associated circumferential crimps, which compress the shank 58 of the electrode around conductor 46. The crimps are not visible in this cross section, but are conventional. Reinforcement member 50 extends along a longitudinal groove 51 machined into the side of the shank of electrode 38. The distal end of reinforcement member 51 is provided with a circumferential ferrule or crimp sleeve 62 which maintains the distal end of reinforcement 51 in a cross bore 64, extending through electrode 38. An internal shoulder 66 engages the crimp sleeve or ferrule 62, maintaining the distal end of reinforcement member 50 coupled to electrode 38. Alternative mechanisms for maintaining the distal end of reinforcement member 50 engaged with electrode 38 may include simply tying a knot in the distal end of the reinforcement member, adhesives, crimps, swages and all other conventional mechanical interconnection mechanisms known to the art. Tine sleeve 36 carrying tines 40 covers the electrode shank 58 and is adhesively coupled to the distal end of the tip ring spacer 34.

In the above-illustrated embodiment, the tensile reinforcement member extends from a conductor associated with a cardioversion or defibrillation electrode. In the context of the disclosed embodiment, this is desirable because the conductor associated with the defibrillation or cardioversion electrode is the largest, highest tensile strength inextensible conductor available in the lead body. However, the present invention may also of course be practiced by extending an inextensible conductor coupled to a ring electrode, sensor or other electrical component located proximal to the distal, tip electrode.

It should also be noted that while the electrode as illustrated in FIG. 4 is a conventional solid metal pacing electrode, any known form of electrode may be substituted therefor. In addition, it is envisioned that some embodiments of the invention, rather than an electrode being the distal electrical component of the lead, a sensor might be substituted. As such, the embodiment disclosed above should be considered exemplary, rather than limiting, with regard to the claims that follow.

In conjunction with the above disclosure, we claim:

1. An implantable electrical lead comprising:
   an elongated lead body having a proximal end and a distal end;
   first and second electrical components located along said lead body, a first of said electrical components located distal to and spaced from a second of said electrical components, said first and second electrical components separated by a portion of said lead body which in turn is fabricated of a pliant, extensible biocompatible insulated material;
   an extensible conductor extending from the proximal end of said lead body to said first electrical component;
   a second, inextensible conductor extending from the proximal end of said lead body to said second electrical component; and
   an inextensible reinforcement member coupled to said second electrical conductor and extending distally from said second electrical component to said first electrical component, said reinforcement member mechanically coupled to said first electrical component, said first electrical component insulated from said second electrical component.

2. A lead according to claim 1 wherein said first electrical component comprises an electrode.

3. A lead according to claim 2 wherein said first and second electrical components comprise electrodes.

4. A lead according to claim 1 wherein said extensible conductor comprises a coiled conductor.

5. A lead according to claim 1 wherein said inextensible conductor comprises a stranded conductor.

6. A lead according to claim 1 wherein said reinforcement member is fabricated of a nonconductive material.

7. A lead according to claim 1, comprising multiple inextensible conductors, wherein said reinforcement member is coupled to the inextensible conductor of highest tensile strength.

8. A lead according to claim 1 wherein said lead body comprises first and second longitudinal lumens, said inextensible conductor extending within a first of said lumens and wherein said reinforcement member extends distally from said inextensible conductor, within said first lumen.

* * * * *